United States Patent
Pyles (10) Patent No.: US 12,290,680 B2
(45) Date of Patent: May 6, 2025

(54) REVERSIBLE ANCHOR FOR SPINAL CORD STIMULATOR LEAD

(71) Applicant: Spiro Medical, Inc., Belleair Bluffs, FL (US)

(72) Inventor: Stephen T. Pyles, Ocala, FL (US)

(73) Assignee: Spiro Medical, Inc., Belleair Bluffs, FL (US)

( * ) Notice: Subject to any disclaimer, the term of this patent is extended or adjusted under 35 U.S.C. 154(b) by 455 days.

(21) Appl. No.: 17/653,914

(22) Filed: Mar. 8, 2022

(65) Prior Publication Data
US 2022/0280781 A1 Sep. 8, 2022

Related U.S. Application Data (60) Provisional application No. 63/158,095, filed on Mar. 8, 2021.

(51) Int. Cl.
*A61N 1/05* (2006.01)
*A61B 90/00* (2016.01)

(52) U.S. Cl.
CPC ............ *A61N 1/0551* (2013.01); *A61B 90/39* (2016.02); *A61N 1/0558* (2013.01)

(58) Field of Classification Search
CPC ..... A61N 1/0551; A61N 1/0558; A61B 90/39
USPC ........................................................ 607/117
See application file for complete search history.

(56) References Cited

U.S. PATENT DOCUMENTS

| | | | |
|---|---|---|---|
| 7,099,718 B1 | 8/2006 | Thacker et al. | |
| 7,640,064 B2 | 12/2009 | Swoyer | |
| 8,260,436 B2 | 9/2012 | Gerber et al. | |
| 8,412,350 B2 | 4/2013 | Bly | |
| 8,509,917 B2 | 8/2013 | Schleicher et al. | |
| 9,265,935 B2 | 2/2016 | Thacker | |
| 9,486,628 B2 * | 11/2016 | Christopherson | A61N 1/3601 |
| 9,861,812 B2 | 1/2018 | Gross et al. | |
| 9,872,981 B2 | 1/2018 | Sparks et al. | |
| 9,981,122 B2 * | 5/2018 | Rawat | A61N 1/36067 |
| 10,369,354 B2 | 8/2019 | Barner | |
| 2005/0096718 A1 * | 5/2005 | Gerber | A61N 1/0558 607/117 |
| 2005/0203602 A1 * | 9/2005 | Wallace | A61N 1/0553 607/122 |
| 2008/0103575 A1 * | 5/2008 | Gerber | A61N 1/0536 607/117 |
| 2011/0257693 A1 * | 10/2011 | Burdulis | A61B 17/8886 606/86 A |

(Continued)

FOREIGN PATENT DOCUMENTS

| | | |
|---|---|---|
| WO | 2013136312 A2 | 9/2013 |
| WO | 2019165108 A1 | 8/2019 |

OTHER PUBLICATIONS

International Search Report for Application No. PCT/US2022/019386 mailed Jun. 20, 2022, 12 pages.

(Continued)

*Primary Examiner* — Michael J Lau
(74) *Attorney, Agent, or Firm* — Merchant & Gould P.C.

(57) ABSTRACT

A percutaneous lead for spinal cord stimulation has a body extending between a distal end and a proximal end. One or more contacts are on the body positioned toward the distal end. At least one anchor is configured to extend from a retracted position to a deployed position to secure the percutaneous lead.

15 Claims, 8 Drawing Sheets

(56) References Cited

U.S. PATENT DOCUMENTS

| | | | |
|---|---|---|---|
| 2013/0013044 A1 | 1/2013 | Thacker et al. | |
| 2013/0245739 A1 | 9/2013 | Arber | |
| 2014/0046347 A1* | 2/2014 | Cully | A61B 17/11 |
| | | | 606/151 |
| 2014/0081362 A1* | 3/2014 | Wicklund | A61N 1/0558 |
| | | | 607/116 |
| 2014/0316402 A1* | 10/2014 | Shah | A61B 18/1206 |
| | | | 606/34 |
| 2015/0272610 A1* | 10/2015 | Pyles | A61B 17/22032 |
| | | | 606/129 |
| 2017/0095658 A1* | 4/2017 | Pyles | A61B 17/22 |
| 2019/0240023 A1* | 8/2019 | Spence | A61F 2/2466 |
| 2019/0255339 A1 | 8/2019 | Lee et al. | |
| 2019/0314633 A1 | 10/2019 | Khalil et al. | |
| 2020/0101291 A1* | 4/2020 | Yakovlev | A61N 2/006 |
| 2020/0306528 A1 | 10/2020 | Linden et al. | |

OTHER PUBLICATIONS

Dublinsky, Lauren, "FDA clears Stimwave's peripheral nerve stimulator system for full-body MR exams," HealthCareBusiness News, pp. 1-4 (2017).
Medgadget Editors, "Sandshark Anchor for Fixating Stimwave's Neurostimulators Cleared in Europe," Medgaget, pp. 1-3 (2017).
Stimwave, Nobel Pain Management & Sports Medicine, www.noblepainandsports.com/stimwave, pp. 1-5 (Accessed Jul. 28, 2021).
Stimwave Techologies, Facebook, www.facebook.com/stimwave, pp. 1-14 (Accessed Jul. 28, 2021).

* cited by examiner

REVERSIBLE ANCHOR FOR SPINAL CORD STIMULATOR LEAD

CROSS-REFERENCE TO RELATED APPLICATIONS

This application claims the benefit of and priority to U.S. Provisional Patent Application No. 63/158,095, filed Mar. 8, 2021, the disclosure of which is herein incorporated by reference in its entirety.

BACKGROUND

Spinal cord stimulation is a medical therapy for treating lower back pain. A spinal cord stimulator is an electronic device that generates an electrical signal that is delivered through a lead into the body of a patient. A lead is typically a catheter type device containing thin wire (e.g., micro sized) that extends from a proximal end to a distal end that allows the spinal cord stimulator to communicate with distal metallic contacts (e.g., electrodes). The distal end of the lead is placed in the epidural space located between the spinal cord and the internal posterior vertebrae. An electrical signal emitted from the distal metallic contacts interacts with spinal cord nerves, and signals the body to reduce or block the pain in various regions of the body.

A typical spinal cord stimulation (SCS) procedure involves two steps. A first step is a temporary trial which is often performed by implanting a temporary spinal cord stimulator to determine the effectiveness of the treatment. If successful, then a second step involves implanting a permanent spinal cord stimulator.

During the SCS trial, an epidural needle is placed in the epidural space and a temporary lead (e.g., a percutaneous lead) is inserted through the needle into the epidural space. The lead is positioned near the posterior spinal cord using the epidural needle. The tip of the temporary lead is positioned within the epidural space. Fluoroscopy is used to show a physician where the temporary lead is located and allows the physician to make sure it is positioned at a desired location. The type of temporary lead used during the trial is a "percutaneous" lead in as much as it is inserted through the skin using an epidural needle. The temporary lead should have a uniform size and shape allowing it to easily slide in and out through the epidural needle.

Once the temporary lead is positioned within the desired location, it is secured to the patient's skin with tape or sutures, or by other means to secure the lead at the point where the SCS lead enters the skin. Stimulator software is connected to the proximal end of the temporary lead allowing the distal contacts to be activated thus generating electrical signals through the lead. The electrical signals can be adjusted to affect the resolution of pain.

During the temporary trial, the patient wears an external stimulator device (having software to control the electrical signals delivered through the lead) for several days or weeks, and then reports back on whether the temporary trial was successful in reducing their pain. If the temporary device relieves the pain, a permanent device can be subsequently implanted.

During the temporary trial, the distal tip of the temporary lead is not secured within the patient's body because it is implanted through an epidural needle, and there is no way to fasten the temporary lead in place without performing a more invasive surgical procedure. Also, the temporary lead will be removed after several days or weeks, and so it is undesirable to perform a surgical incision fastening technique near the spine that would prevent removal or cause tissue damage upon removal.

As a result, the tip of the temporary lead often moves out of the desired location which can reduce, or even eliminate, the therapeutic benefit from spinal cord stimulation during the temporary trial because the electrical signal from the stimulator does not reach the desired location or migrates from the desired location. Sometimes the temporary lead moves out of position as soon as the patient moves off of the surgical table after the temporary lead has been placed. This can happen because trial leads are adhered to the skin which is a considerable distance from the area where the lead enters the epidural space, the body is flexible, and even though the trial lead is fixed at the skin surface, the patient's body, which includes skin, fat, muscle, and other soft tissues, can move and pull or press on the trial lead, causing the distal end of the trial lead to move out of position.

SUMMARY

In general terms, the present disclosure relates to an anchor device that can be used to temporarily anchor a percutaneous trial or permanent lead of a spinal cord stimulator within the body of a patient in close approximation to the lead's entry point into the epidural space. In one possible configuration, the anchor device is retracted when being inserted into the patient's body, and is then extended once the lead is positioned in the desired location. Various aspects are described in this disclosure, which include, but are not limited to, the following aspects.

In one aspect, a percutaneous lead for spinal cord stimulation comprises: a body extending between a distal end and a proximal end; at least one contact on the body positioned toward the distal end; at least one anchor mounted on the body, the at least one anchor configured to extend between a retracted position and a deployed position to secure the percutaneous lead outside of an epidural space and adjacent to an exterior part of the spine; and at least one marker visible in fluoroscopy imaging to identify a location of the at least one anchor outside of the epidural space.

In another aspect, an anchoring system comprises: a trial percutaneous lead extending between a distal end and a proximal end, the distal end having one or more contacts configured for placement inside an epidural space; and an anchor separate from the trial percutaneous lead, the anchor configured for placement outside of the epidural space and to apply a pressure on the trial percutaneous lead without attaching to the trial percutaneous lead, the pressure preventing the distal end of the trial percutaneous lead from migrating inside the epidural space.

In another aspect, a method of using a percutaneous lead comprises: positioning a distal end that includes at least one contact of the percutaneous lead into a desired location of an epidural space of the spine; selecting one or more anchors for deployment on the percutaneous lead, the one or more anchors selected by viewing at least one of an anterior, a posterior, and a lateral fluoroscopic view showing the position of markers aligned with locations of the one or more anchors relative to the epidural space and an exterior part of the spine; and deploying the one or more selected anchors to anchor the percutaneous lead in the deep facia or ligamentum tissue of the spine to prevent the distal end of the percutaneous lead from moving out of the desired location within the epidural space.

In another aspect, a percutaneous lead for spinal cord stimulation comprises: a body extending between a distal end and a proximal end; at least one contact on the body positioned toward the distal end; and a plurality of anchors on the body, each anchor being individually controlled between a retracted position and a deployed position to secure the percutaneous lead outside of an epidural space and adjacent to an exterior part of the spine.

In another aspect, a percutaneous lead for spinal cord stimulation comprises: a body extending between a distal end and a proximal end; at least one contact mounted to the body at the distal end; at least one anchor mounted to the body, the at least one anchor controlled to operate between a retracted position and a deployed position to secure the percutaneous lead outside of an epidural space and adjacent to an exterior part of the spine; and at least one marker visible in fluoroscopy imaging, the at least one marker marking a location of the at least one anchor on the body.

In another aspect, a method of using a percutaneous lead comprises: positioning a distal end that includes at least one contact of the percutaneous lead into a desired location of an epidural space of the spine; selecting one or more anchors for deployment on the percutaneous lead, the one or more anchors selected by viewing anterior, posterior, and lateral fluoroscopic views that show the position of the anchors relative to the epidural space and an exterior part of the spine; and deploying the one or more selected anchors to anchor the percutaneous lead in the deep facia or ligamentum tissue of the spine to prevent the distal end of the percutaneous lead from moving out of the desired location within the epidural space.

In another aspect, an anchoring system comprises: a trial percutaneous lead extending between a distal end and a proximal end, the distal end having one or more contacts configured for placement inside an epidural space; and an anchor separate from the trial percutaneous lead, the anchor configured for placement outside of the epidural space to apply a pressure on the trial percutaneous lead without attaching to the trial percutaneous lead, the pressure preventing the distal end of the trial percutaneous lead from migrating inside the epidural space.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
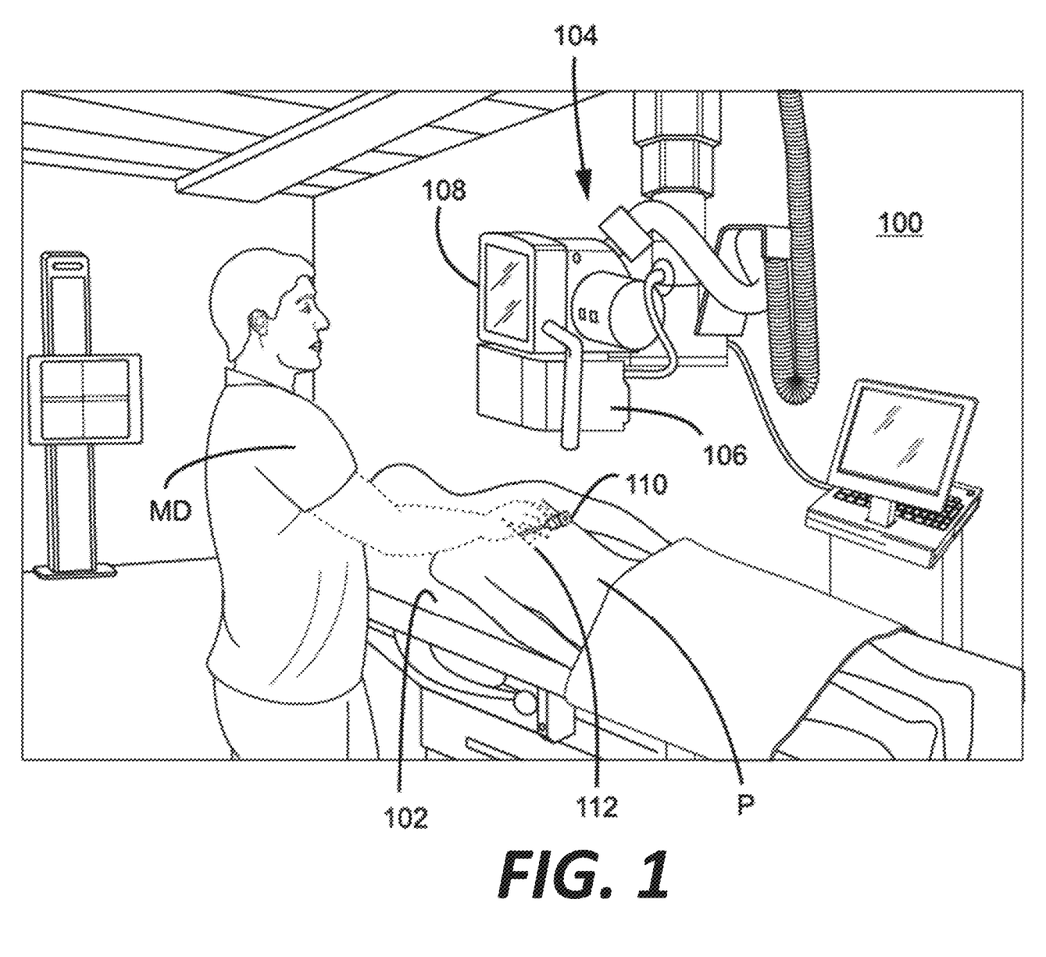
FIG. 1 illustrates an example of a system for performing a procedure to implant one or more percutaneous leads for spinal cord stimulation.

FIG. 1 illustrates an example system 100 for performing a procedure to implant one or more leads for spinal cord stimulation. In some examples, an epidural needle 110 is used to implant temporary percutaneous leads for a trial spinal cord stimulation procedure. In alternative examples, the epidural needle 110 is used to implant permanent percutaneous leads. The system 100 includes a table 102 on which a patient P rests face down. The patient P's back is exposed for a physician MD to insert the epidural needle 110.

The epidural needle 110 can be a 13G or 14G needle that is inserted into the skin, and through the paravertebral muscles until it reaches the lamina next to the spinous process located just below a selected target location in the epidural space the patient P's spine. The epidural needle 110 is then advanced through the ligamentum flavum and into the epidural space.

The system 100 includes a fluoroscopy system 104 that has at least an imaging device 106 that captures fluoroscopy images (i.e., X-ray images) of the patient P's spine, and a display device 108 that displays the fluoroscopy images for viewing by the physician MD. The physician MD can view the fluoroscopy images while inserting the epidural needle 110 into the patient P's epidural space, and while implanting the leads into the patient P's epidural space.

As an illustrative example, the physician MD inserts the epidural needle 110 into the epidural space of the patient P's spine, and thereafter threads one or more insulated wire leads through the epidural needle 110 to implant the distal ends of the leads into the epidural space. The leads are implanted into the epidural space to ensure that the leads are effective in providing desired pain relief. The angle at which the epidural needle 110 is inserted into the patient P's spine can determine whether the leads successfully reach the posterior epidural space.

In the example illustrated in FIG. 1, a pattern of markings 112 are drawn on the patient P's back. The pattern of markings 112 are used by the physician MD as a path for inserting the epidural needle 110 into the patient P's spine at the correct angle. The pattern of markings 112 is drawn by using a device described in more detail in U.S. patent application Ser. No. 17/113,232, filed Dec. 7, 2020, the entirety of which is hereby incorporated by reference. In some examples, the physician MD can insert the epidural needle 110 into the patient P's spine without using the markings 112, such that the markings 112 are optional.

Figure 2:
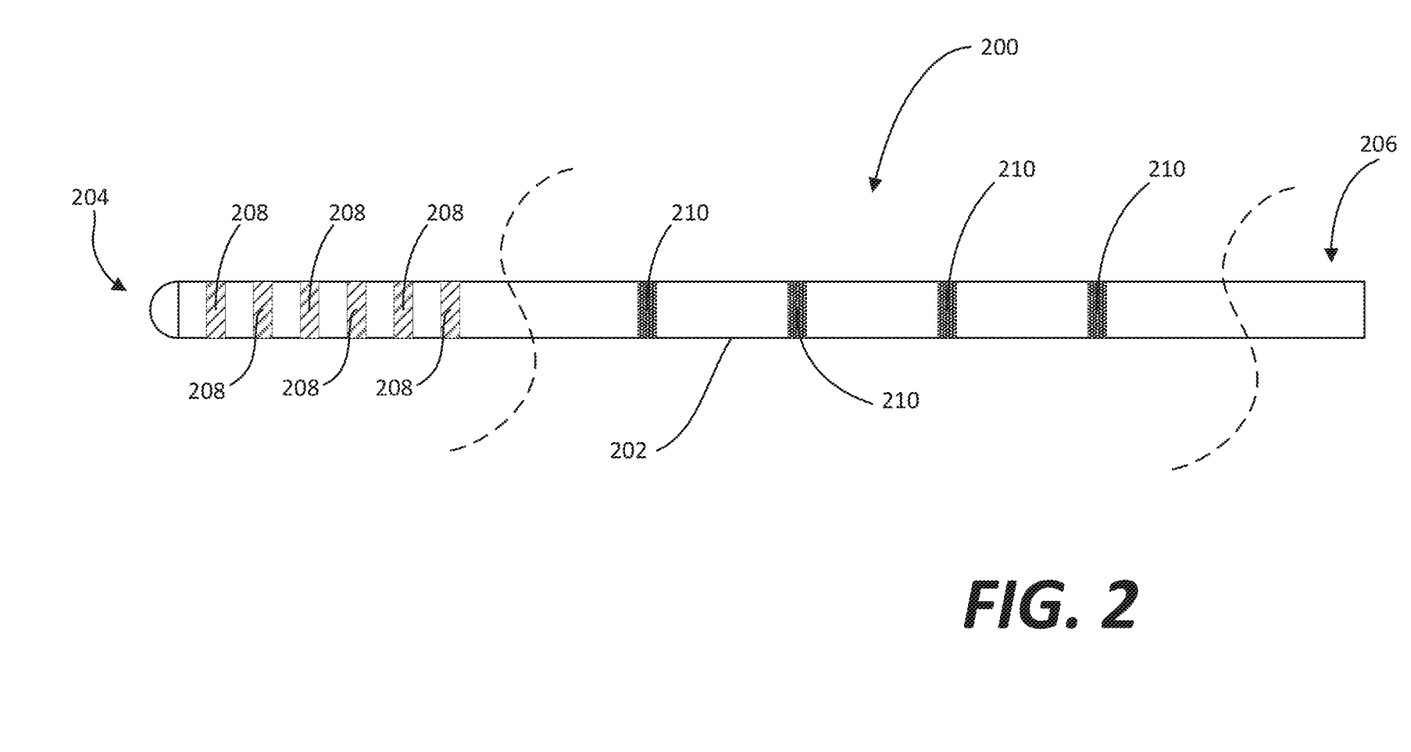
FIG. 2 illustrates an example of a percutaneous lead for spinal cord stimulation with one or more anchors each in a retracted position.
Figure 4:
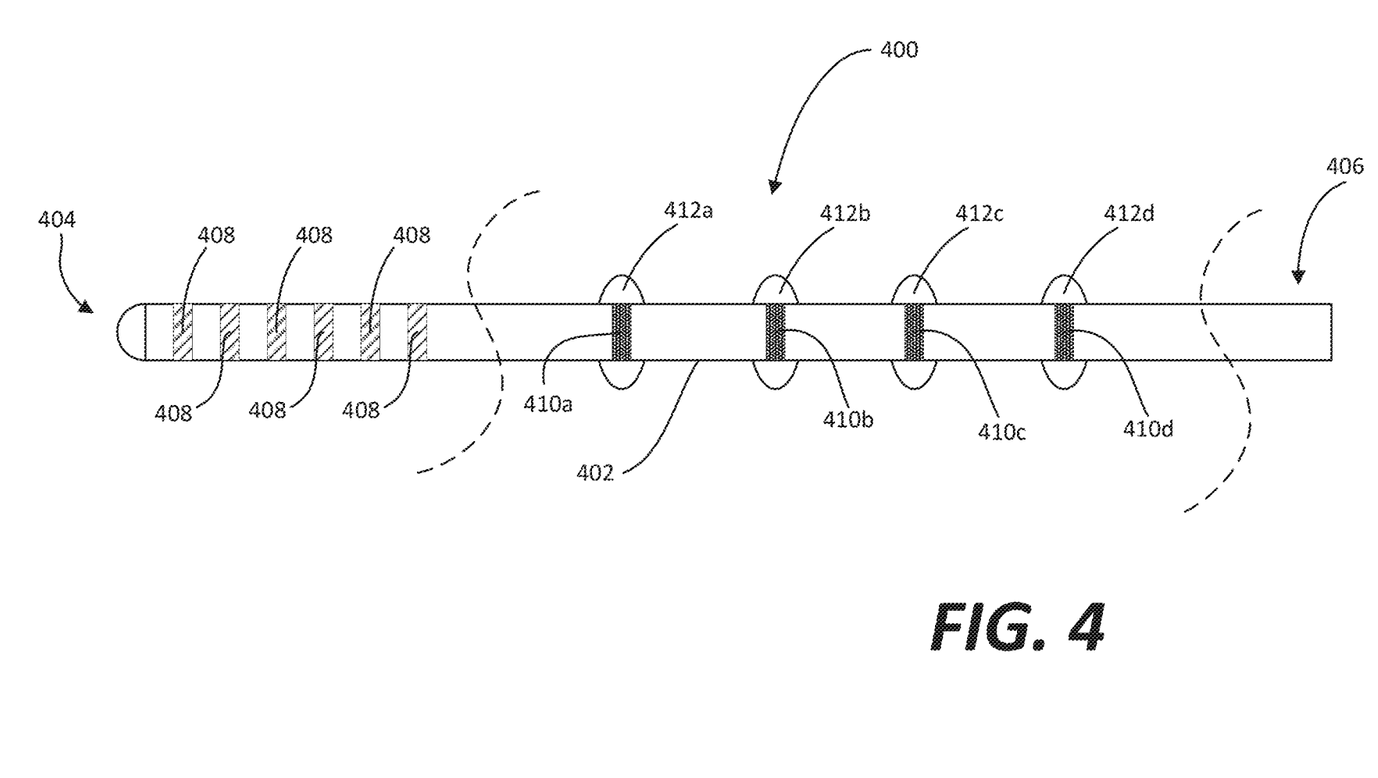
FIG. 4 illustrates an example of the percutaneous lead of FIG. 2 for spinal cord stimulation with one or more anchors in a deployed position.
Figure 5:
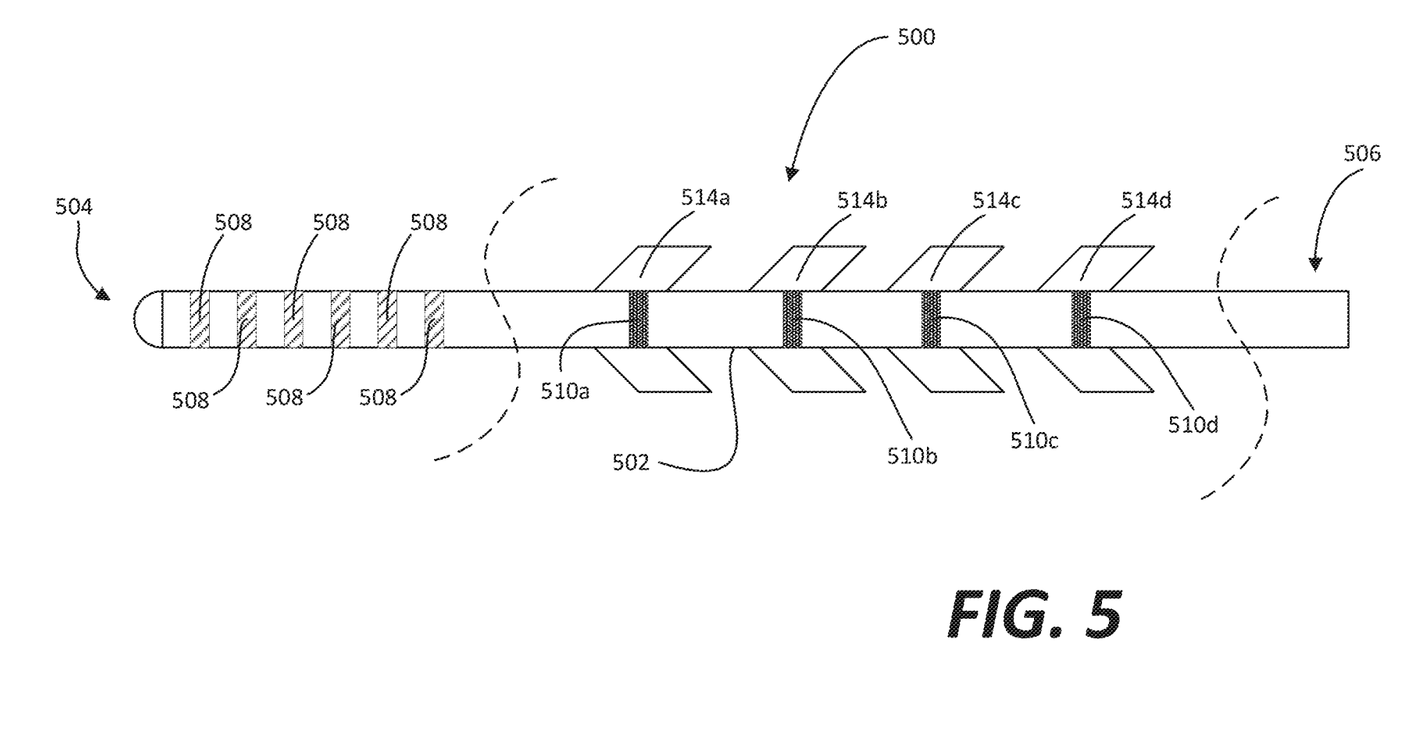
FIG. 5 illustrates another example of the percutaneous lead of FIG. 2 for spinal cord stimulation with one or more anchors in a deployed position.
Figure 6:
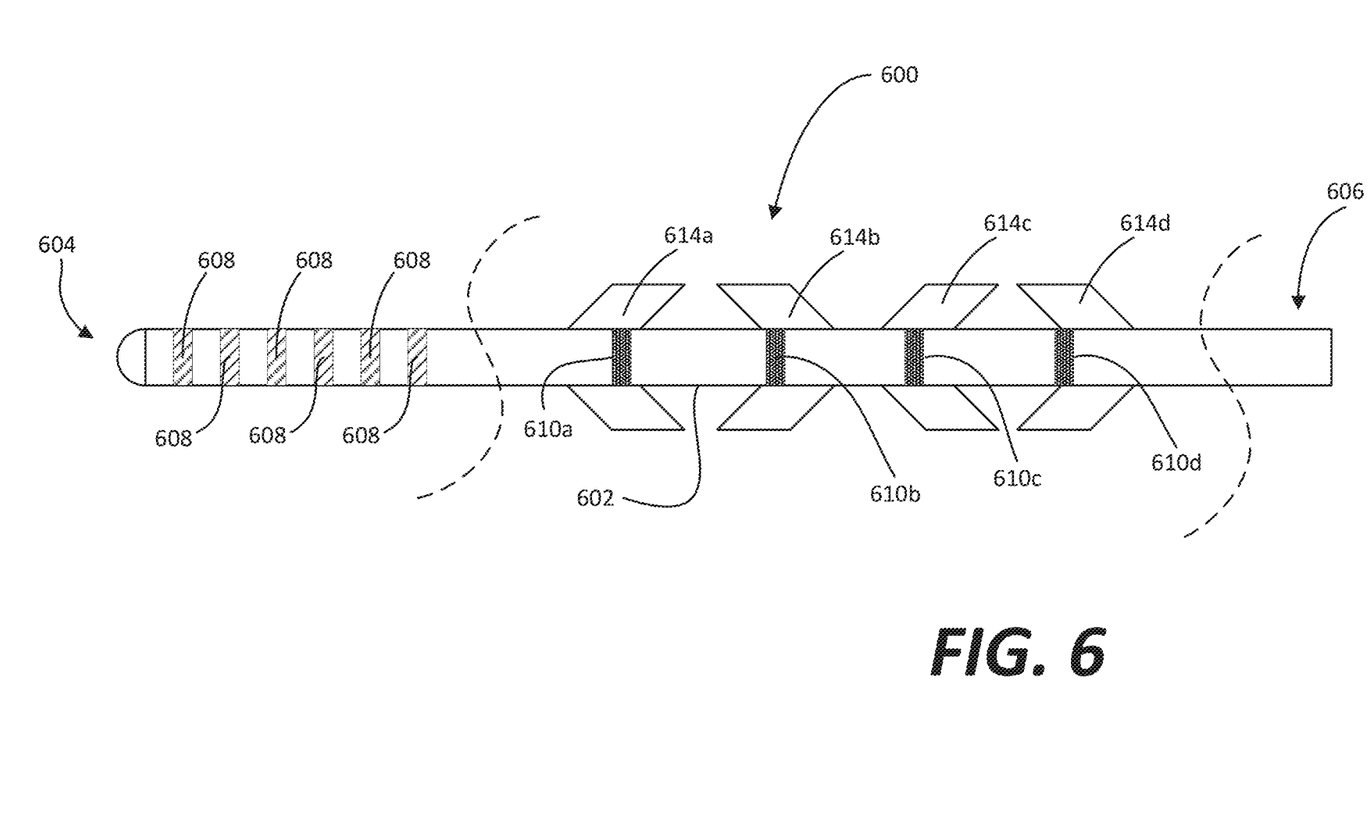
FIG. 6 illustrates another example of the percutaneous lead of FIG. 2 for spinal cord stimulation with one or more anchors in a deployed position.

FIG. 2 illustrates an example of a percutaneous lead 200 for spinal cord stimulation with one or more anchors in a retracted position. Examples of anchors in the deployed position are shown in FIGS. 4-6 and will be described in more detail. In some examples, the percutaneous lead 200 is a temporary lead that is implanted during a trial for spinal cord stimulation. Alternatively, the percutaneous lead 200 can be permanently implanted for spinal cord stimulation after completion of a successful temporary trial.

The percutaneous lead 200 has a body 202 that extends between a distal end 204 and a proximal end 206. The body 202 has a tubular shape of a uniform diameter and circumference that allows the percutaneous lead 200 to easily slide through an epidural needle. The distal end 204 is configured for placement inside the epidural space of the spine. The proximal end 206 is configured to connect to a stimulator device that generates electrical signals.

The percutaneous lead 200 includes one or more contacts 208 positioned toward the distal end 204 which, as described above, is configured for placement inside the epidural space of the spine. The contacts 208 are examples of electrodes such as electrical conductors. Each contact 208 is configured to receive electrical signals from the stimulator device and to release the electrical signals in the epidural space for interaction with one or more nerves to reduce or block the pain sensations. In the example illustrated in FIG. 2, the contacts 208 are evenly spaced apart. The number of contacts 208 included on the percutaneous lead 200 may vary. For example, the percutaneous lead 200 may include at least one contact, or may include a plurality of contacts such as 5, 10, 15, 20, or more contacts.

Figure 3:
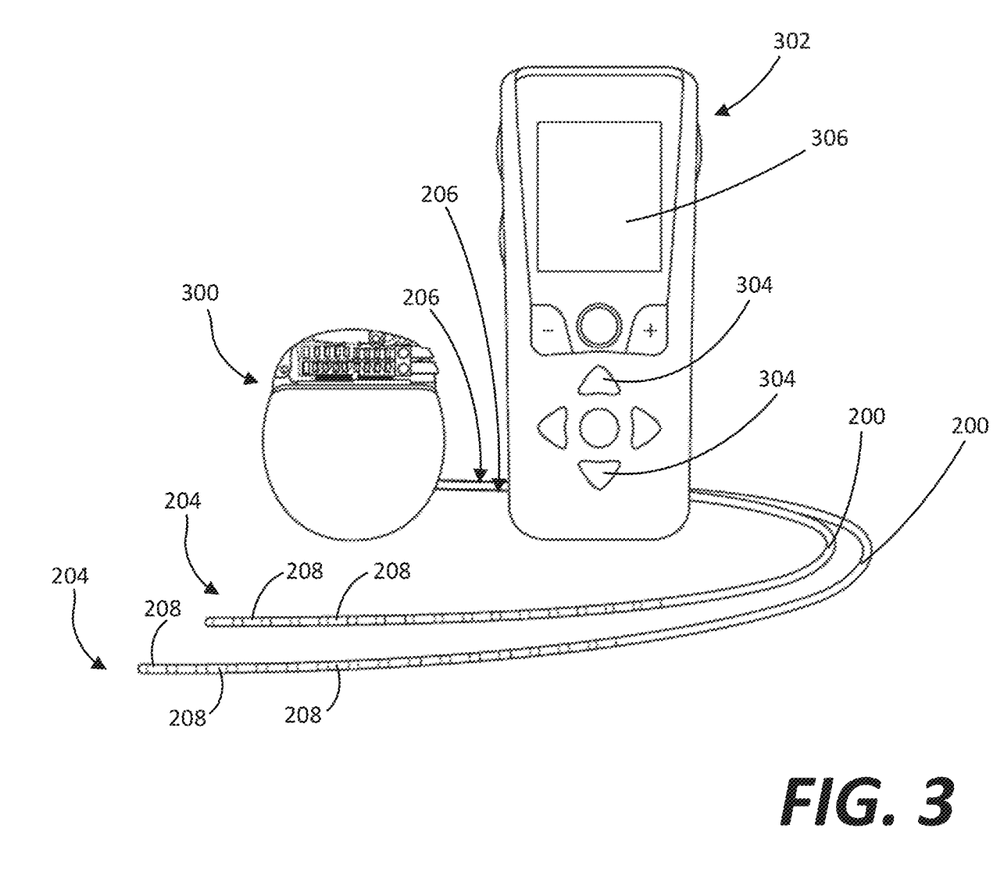
FIG. 3 illustrates the percutaneous lead of FIG. 2 connected to a stimulator device that generates and sends electrical signals through the percutaneous lead, and an external controller that can be used to adjust the electrical signals from the stimulator device.

FIG. 3 illustrates percutaneous leads 200 connected to a stimulator device 300 that generates and sends electrical signals through the percutaneous leads 200. In the example illustrated in FIG. 3, two percutaneous leads are connected to the stimulator device 300.

As shown in FIG. 3, the proximal end 206 of each percutaneous lead 200 is connected to the stimulator device 300. In some examples, the proximal ends 206 of the percutaneous leads 200 are configured to extend outside of the patient P's body for connection to the stimulator device 300. In such examples, the stimulator device 300 is not an implanted device, but is rather carried or worn by the patient P such as during a temporary trial for spinal cord stimulation. Alternatively, the stimulator device 300 can be implanted under the skin of the patient P such as from a permanent spinal cord stimulation procedure such that the proximal ends 206 of the percutaneous leads 200 do not extend outside of the patient P's body.

FIG. 3 further shows an external controller 302 that can be used to adjust the electrical signals that are generated by the stimulator device 300. The external controller 302 can wireless communicate with the stimulator device 300 to adjust the frequency and strength of the electrical signals that are generated by the stimulator device 300. The external controller 302 includes one or more input buttons 304 and a display screen 306. The input buttons 304 can be selected by the patient P to increase the frequency and/or strength of the electrical signals to provide stronger pain relief, or to decrease the frequency and/or strength of the electrical signals to provide less pain relief, based on the degree of lower back pain experienced by the patient P.

Referring back to FIG. 2, the percutaneous lead 200 includes one or more markers 210 that are visible in the fluoroscopy imaging generated on the display device 108 (see FIG. 1). For example, each marker 210 can be made of stainless steel or similar materials. In the example illustrated in FIG. 2, the markers 210 are evenly spaced apart, and are positioned along the length of the body 202. Each marker 210 marks the location of an anchor on the body 202.

Referring now to FIGS. 1 and 2, the physician MD can see the markers 210 on the display device 108 to identify the locations of the anchors on the percutaneous lead 200 when implanting the lead. Advantageously, once the distal end 204 is positioned inside the epidural space at a desired location, the physician MD can identify one or more anchors at an appropriate location outside of the epidural space for deployment. When deployed, the one or more anchors secure the percutaneous lead 200 inside the patient's body such that the distal end 204 does not move out of the desired position after the percutaneous lead 200 has been implanted.

In some examples, the percutaneous lead 200 is sized such that the distance of the markers 210 (and corresponding anchors) from the distal end 204 is configurable based on a type of desired pain relief and size of the patient. Thus, a plurality of percutaneous leads may be developed with different spacing for the one or more anchors based on desired patient outcomes.

In some examples, the markers 210 (and corresponding anchors) are positioned along a length of the body 202 such that a first marker 210a is positioned about 10-40 cm from the distal end 204. In some examples, the first marker 210a is positioned about 20-30 cm from the distal end 204. In some examples, the markers 210 are evenly spaced apart by about 5 cm.

FIG. 4 illustrates an example of the percutaneous lead 400 with one or more anchors 412 in a deployed position. The percutaneous lead 400 can be used as a temporary or a permanent lead. In FIG. 4, the one or more anchors 412 are balloons that can inflate to a predetermined diameter in the deployed position to secure the percutaneous lead 400 inside the patient's body. For example, the one or more anchors 412 can be inflated with a gas, such as air, or a liquid such as a saline solution. In some examples, the one or more anchors 412 are inflated to have a dimeter that is 2-3 times larger than the diameter of a body 402 of the lead.

In some examples, the one or more anchors 412 are inflated with a material visible in the fluoroscopy imaging generated on the display device 108 (see FIG. 1). The material can be a radiopaque substance such as x-ray dye. As another example, the one or more anchors 412 can be inflated with a saline solution having metal particles that are visible in the fluoroscopy imaging. Advantageously, this can provide visual confirmation that the one or more anchors 412 are deployed at a desired location outside of the epidural space of the spine.

In some examples, the proximal end 406 of the percutaneous lead 400 is connected to an external controller that can be used to inflate and deflate the one or more anchors 412. In some examples, each anchor 412 has its own valve that can be separately opened and closed such that each anchor 412 is individually deployable along the length of the percutaneous lead 400. In other examples, each anchor 412 is connected to the device by a separate line such that each anchor 412 is individually deployable along the length of the percutaneous lead 400.

The one or more anchors 412 are inflatable and deflatable between the retracted and deployed positions, respectively. For example, once the contacts 408 of the percutaneous lead 400 are positioned inside the epidural space at a desired location, the one or more anchors 412 can be inflated into the deployed position to fix the percutaneous lead 400 to prevent the distal end 404 from moving out of place. In some examples, a combination of any two or three of the anchors 412 are inflated to anchor the percutaneous lead 400 in the deployed position.

Thereafter, the anchors 412 can at a later date be deflated into the retracted position (e.g., see FIG. 2) to allow the percutaneous lead 400 to be removed from the patient P's body without causing tissue damage upon removal. For example, the anchors 412 can be deflated into the retracted position upon completion of a temporary trial for spinal cord stimulation such as after several days or weeks from the date the percutaneous lead 400 was implanted in the patient P's body. In other instances, the anchors 412 can be deflated into the retracted position several years from the date the percutaneous lead 400 was implanted in the patient P's body such as when the percutaneous lead 400 is used for a permanent spinal cord stimulator.

The one or more anchors 412 reduce the time required to implant the percutaneous lead 400 because the anchors eliminate the need for an invasive surgical procedure to secure the percutaneous lead 400 to the patient P's body such as by suturing, which relies on good surgical technique. Additionally, the one or more anchors 412 reduce the time required to remove the percutaneous lead 400 because the physician MD will not have to undue the suturing in order to remove the percutaneous lead 400. Instead, the physician MD can simply deflate the one or more anchors 412 from the deployed position to the retracted position, and then pull the percutaneous lead 400 out of the patient P's body without causing tissue damage upon removal.

In the example illustrated in FIG. 4, the percutaneous lead 400 is shown as having four anchors 412a-412d. The number of anchors 412 included on the percutaneous lead 400 may vary such that the percutaneous lead 400 is not limited to the number and arrangement of anchors shown in FIG. 3. For example, the percutaneous lead 400 may include at least one anchor 412, or may include a plurality of anchors 412 such as 2, 3, 4, 5, or more anchors 412.

As shown in FIG. 4, the locations of markers 410a-410d align with the locations of the anchors 412a-412d. For example, a location of a first marker 410a aligns with a location of a first anchor 412a, a location of a second marker 410b aligns with a location of a second anchor 412b, a location of a third marker 410c aligns with a location of a third anchor 412c, a location of a fourth marker 410d aligns with a location of a fourth anchor 412d, and so on. The markers 410a-410d, which are made from a material visible in the fluoroscopy images generated on the display device 108 (see also FIG. 1), can be used by the physician MD to identify the locations of the anchors 412a-412d that are positioned along the length of the percutaneous lead 400 whether the anchors 412a-412d are in the retracted position or deployed position.

The percutaneous lead 400 allows the physician MD to individually select one or more anchors or one or more combinations of anchors for deployment at a desired location outside of the epidural space to secure the percutaneous lead 400 inside the body of the patient P. For example, the physician MD can individually select one or more anchors or one or more combinations of anchors to anchor the percutaneous lead 400 in the deep facia or ligamentum tissue adjacent to an exterior part of the spine. Advantageously, this can prevent the distal end 404 of the percutaneous lead 400 from moving out of a desired location within the epidural space, while also reducing the impact of the one or more anchors on the spinal cord, regardless of whether the percutaneous lead 400 is used as a temporary or a permanent lead.

As described above, each anchor 412a-412d is individually deployable along the length of the percutaneous lead 400. For example, a first anchor 412a can be selected by the physician MD for deployment without also having to deploy a second anchor 412b, a third anchor 412c, or a fourth anchor 412d. Similarly, the second anchor 412b can be selected by the physician MD for deployment without also having to deploy the first anchor 412a, the third anchor 412c, or the fourth anchor 412d. As another example, the third anchor 412c can be selected by the physician MD for deployment without also having to deploy the first anchor 412a, the second anchor 412b, or the fourth anchor 412d. As yet a further example, the fourth anchor 412d can be selected by the physician MD for deployment without also having to deploy the first anchor 412a, the second anchor 412b, or the third anchor 412c. As noted above, the number of anchors 412 included on the percutaneous lead 400 may vary such that the percutaneous lead 400 can included additional anchors that are individually deployable, or may include a single anchor that can be deployed to secure the percutaneous lead 400.

Additionally, multiple combinations of anchors can be selected by the physician MD for deployment. For example, the first and second anchors 412a, 412b can be selected by the physician MD for deployment without also having to deploy the third and fourth anchors 412c, 412d. Similarly, the third and fourth anchors 412c, 412d can be deployed without also having to deploy the first and second anchors 412a, 412b. As another example, the second and third anchors 412b, 412c can be deployed without also having to deploy the first anchor 412a or the fourth anchor 412d. Additional combinations of anchors 412 that can be deployed are possible.

FIG. 5 illustrates another example of a percutaneous lead 500 for spinal cord stimulation with one or more anchors 514 in a deployed position. The percutaneous lead 500 is similar to the percutaneous leads 200, 400 shown in FIGS. 2 and 4, respectively. The percutaneous lead 500 can be used as a temporary or a permanent lead. The percutaneous lead 500 includes a body 502 that extends between a distal end 504 and a proximal end 506, one or more contacts 508, and one or more markers 510. The percutaneous lead 500 differs in that the anchors 514a-514d are tines that are remotely activated to extend between the retracted and deployed positions by signals received from an external controller.

The anchors 514a-514d are an integral part of the body 502. In some examples, the anchors 514a-514d are extendible to have a dimeter that is 2-3 times larger than the diameter of a body 502 of the percutaneous lead 500 when in the deployed position. When the anchors 514a-514d are in the retracted position, the anchors 514a-514d have a dimeter that is substantially equal to the diameter of the body 502. In some examples, the anchors 514a-514d have a dimeter equal to the diameter of the body 502 when in the retracted position.

In some examples, the external controller is not physically connected to the percutaneous lead 500 such that the signals that active the anchors 514a-514d are received wirelessly. For example, the external controller can be a mobile electronic device that is operated by the physician MD, and that can send wireless signals to extend the anchors 514a-514d into the deployed position. As an illustrative example, the signals for controlling the anchors 514a-514d can include, without limitation, Bluetooth, Wi-Fi, RFID, Near-Field Communication (NFC), and the like. Additionally, the anchors 514a-514d can be controlled through a magnetic field generated by the external controller to extend and retract the anchors 514a-514d.

In alternative examples, the external controller is connected to the proximal end 506 of the percutaneous lead 500, and can send signals to extend and retract the anchors 514a-514d through a wired connection. In yet further examples, the anchors 514a-514d can be extended and retracted through mechanical means such as through a push-pull mechanism that causes the anchors 514a-514d to extend and retract. Additional configurations are contemplated.

In the example shown in FIG. 5, the percutaneous lead 500 is shown as having four anchors 514a-514d. The number of anchors 514 included on the percutaneous lead 500 may vary such that the percutaneous lead 500 is not limited to the number and arrangement of anchors shown in FIG. 5. For example, the percutaneous lead 500 may include at least one anchor 514, or may include a plurality of anchors 514 such as 2, 3, 4, 5, or more anchors 514. Also, the anchors 514a-514d are shown as extending beyond at least two opposite sides of the body 502 of the percutaneous lead 500 when in the deployed position. In alternative examples, the anchors 514a-514d can extend from only one side of the body 502 when in the deployed position.

The locations of the markers 510a-510d align with the locations of the anchors 514a-514d. For example, a location of a first marker 510a aligns with a location of a first anchor 514a, a location of a second marker 510b aligns with a location of a second anchor 514b, a location of a third marker 510c aligns with a location of a third anchor 514c, a location of a fourth marker 510d aligns with a location of a fourth anchor 514d, and so on. The markers 510a-510d are made from a material visible in the fluoroscopy images generated on the display device 108 (see FIG. 1), such that the markers 510a-510d can be used by the physician MD to identify the locations of the anchors 514a-514d whether in the retracted position or deployed position.

In some examples, the one or more anchors 514a-514b are made from a radiopaque material that is visible in the fluoroscopy imaging generated on the display device 108 (see FIG. 1). In such examples, the markers 510a-510d are not needed because the one or more anchors 514a-514b are visible in the fluoroscopy imaging whether in the retracted position or in the deployed position. Additionally, such examples can further provide visual confirmation as to whether that the one or more anchors 514a-514d are in the retracted or deployed positions.

The percutaneous lead 500 allows the physician MD to individually select one or more of the anchors 514a-514d or one or more combinations of the anchors 514a-514d for deployment at a desired location outside of the epidural space to secure the percutaneous lead 500 inside the body of the patient P. In some examples, a combination of any 2 or 3 of the anchors 514a-514d are extendible to anchor the percutaneous lead 500.

The physician MD can individually select one or more of the anchors 514a-514d or one or more combinations of the anchors 514a-514d to anchor the percutaneous lead 500 in the deep facia or ligamentum tissue adjacent to an exterior part of the spine. This can prevent the distal end 504 of the percutaneous lead 500 from moving out of a desired location within the epidural space, and reduce the impact of the one or more anchors on the spinal cord, regardless of whether the percutaneous lead 500 is used as a temporary or a permanent lead.

In the example shown in FIG. 5, the anchors 514a-514d have a unidirectional arrangement such that the anchors 514a-514d are each oriented in the same direction when in the deployed position. The unidirectional arrangement can resist migration of the percutaneous lead 500 in a direction opposite the insertion path of the percutaneous lead 500.

FIG. 6 illustrates another example of a percutaneous lead 600 for spinal cord stimulation with one or more anchors 614a-614b in the deployed position. The percutaneous lead 600 is similar to the percutaneous lead 500 shown in FIG. 5. The percutaneous lead 600 can be used as a temporary or a permanent lead. The percutaneous lead 600 includes a body 602 that extends between a distal end 604 and a proximal end 606, one or more contacts 608, and one or more markers 610. The percutaneous lead 600 differs from the percutaneous lead 500 in that the anchors 614a-614d have a bidirectional arrangement such that the anchors 614a-614d are oriented in different directions when in the deployed position.

As shown in the illustrative example provided in FIG. 6, the first and third anchors 614a, 614c are orientated in a direction toward the proximal end 606 to prevent the percutaneous lead 600 from sliding in the direction toward the proximal end 606 when the first and third anchors 614a, 614c are in the deployed position. The second and fourth anchors 614b, 614d are orientated in a direction toward the distal end 604 to prevent the percutaneous lead 600 from sliding in the direction toward the distal end 604 when the second and fourth anchors 614b, 614d are in the deployed position. Thus, the bidirectional orientation resists migration of the percutaneous lead 400 in both directions relative to the insertion path of the lead.

In FIG. 6, the percutaneous lead 600 is shown as having four anchors 614a-614d. The number of anchors 614 included on the percutaneous lead 600 may vary such that the percutaneous lead 600 is not limited to the number and arrangement of anchors shown in FIG. 6.

Figure 7:
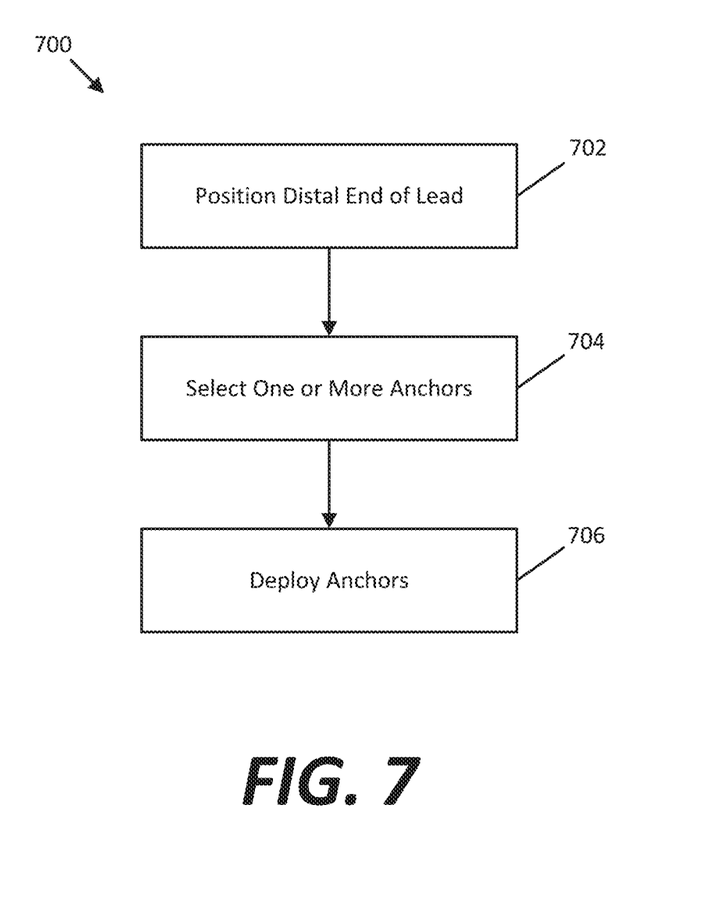
FIG. 7 illustrates an example of a method of using a percutaneous lead according to any one of the examples of the percutaneous leads shown in FIGS. 1-6.

FIG. 7 illustrates a method 700 of using a percutaneous lead according to any one of the examples of the percutaneous leads shown in FIGS. 2-6. The method 700 includes a step 702 of positioning the distal end that includes at least one contact of the percutaneous lead into a desired location of the epidural space of the spine to provide desired lower back pain relief. The percutaneous lead can be used as a temporary or a permanent lead. As described above, an epidural needle can be used to insert the percutaneous lead into the epidural space. In step 702, the one or more anchors on the percutaneous lead are in the retracted position such that the percutaneous lead has a tubular shape of a uniform diameter and circumference that allows the percutaneous lead to slide through the epidural needle to reach the epidural space.

Next, the method 700 includes a step 704 of selecting one or more anchors for deployment on the percutaneous lead. The one or more anchors can be selected by viewing anterior, posterior, and lateral fluoroscopic views that show the position of the anchors relative to the epidural space and spine. Optimally, the selected anchors are outside the epidural space and the spinal canal, and are adjacent to the exterior part of the spine.

Next, the method 700 includes a step 706 of deploying the one or more selected anchors. The anchors when deployed are used for anchoring the percutaneous lead in the deep facia or ligamentum tissue of the spine to prevent the distal end of the percutaneous lead from moving out of or migrating away from the desired location within the epidural space.

Step 706 can include using an external controller to remotely deploy the one or more selected anchors. For example, the external controller that can be used to inflate the one or more selected anchors by individually opening one or more valves associated with each of the one or more selected anchors or by connecting each of the one or more selected anchors to a separate line such that each anchor is individually inflatable on the body of the percutaneous lead.

In some examples, the external controller can be used to send wireless signals to activate the one or more selected anchors to extend into the deployed position such as by using a wireless connection including, without limitation, Bluetooth, Wi-Fi, RFID, Near-Field Communication (NFC), and the like. In some examples, the external controller activates the one or more selected anchors by generating a magnetic field that causes the one or more selected anchors to extend into the deployed position. In some examples, the external controller can send signals through a wired connection to extend the one or more selected anchors into the deployed position. In yet further examples, the anchors can be extended into the deployed position through mechanical means such as through a push-pull mechanism.

Figure 8:
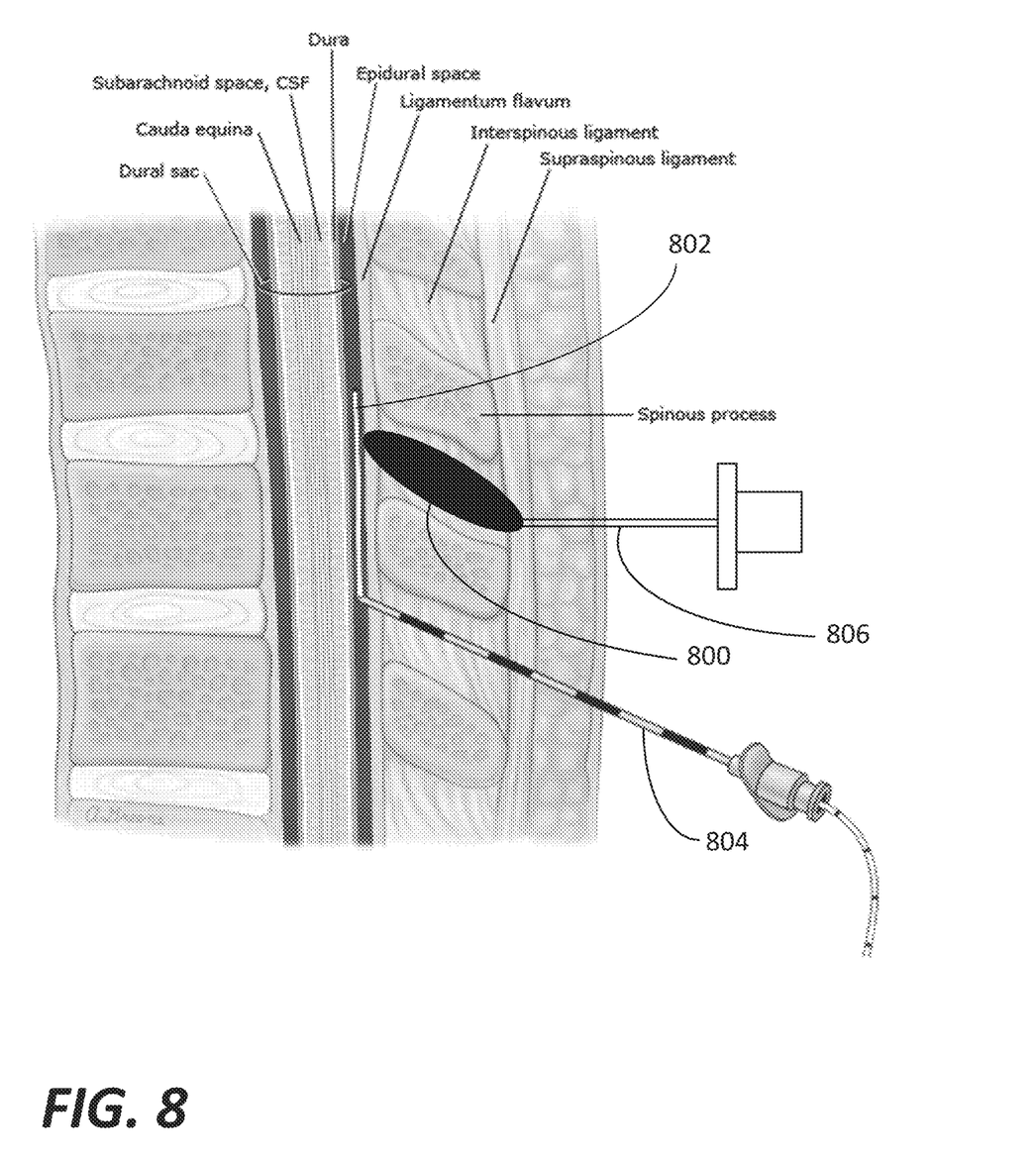
FIG. 8 illustrates another example of an anchor for temporarily fixing a trial percutaneous lead inside the epidural space of the spine.

FIG. 8 illustrates another example of an anchor 800 for temporarily fixing a trial percutaneous lead 802 inside the epidural space of the spine. In the example shown in FIG. 8, the trial percutaneous lead 802 is a neuro-stimulator lead for spinal cord stimulation. The trial percutaneous lead 802 is inserted into the epidural space by an epidural needle 804. As shown in FIG. 8, the epidural needle 804 is inserted into the skin, through the paravertebral muscles of the spinous process, through the ligamentum flavum, and into the epidural space.

In some examples, the anchor 800 is a temporary anchor for the trial neuro-stimulator lead. The anchor 800 is inserted through an introducer needle 806. The anchor 800 can be used to prevent movement or migration of the trial percutaneous lead 802 inside the epidural space without attaching to the trial percutaneous lead 802 or contacting the trial percutaneous lead 802.

In one example, the anchor 800 is a balloon that is inflatable outside of the epidural space to apply pressure on the trial percutaneous lead 802 that prevents the trial percutaneous lead 802 from moving or migrating while inserted inside the epidural space. In some examples, the anchor 800 is inflated with a gas, such as air, or a liquid such as a saline solution.

In some examples, the anchor 800 is inflated with a material visible in the fluoroscopy imaging generated on the display device 108 (see FIG. 1). The material can be a radiopaque substance such as x-ray dye. In further examples, the anchor 800 can be inflated with a saline solution having metal particles that are visible in the fluoroscopy imaging. The material visible in the fluoroscopy imaging can provide visual confirmation that the anchor 800 is properly positioned outside of the epidural space for applying an appropriate amount of pressure on the trial percutaneous lead 802 in the correct location.

The anchor 800 is also reversible. For example, the anchor 800 is deflatable to release the pressure applied onto the trial percutaneous lead 802 allowing the trial percutaneous lead to be removed from the epidural space, such as after completion of a temporary trial for spinal cord stimulation. Thereafter, the anchor 800 can be removed from the patient's body.

In some additional embodiments, the anchor 800 includes an absorbable material that is naturally absorbed by the body after the anchor 800 is deployed to secure the trial percutaneous lead 802 inside the epidural space. In such examples, the anchor 800 does not need to be physically retracted or removed. In some further examples, the absorbable material includes an antibiotic to provide an additional therapeutic effect.

In further examples, an anchor can be held on the epidural needle that is used to insert a trial percutaneous lead into the epidural space. In such examples, when the trial percutaneous lead is positioned at a desired location within the epidural space, the lead can be pushed off the epidural needle and onto the trial percutaneous lead. In this manner, the anchor can be used to temporarily fix the trial percutaneous lead inside the epidural space during a trial spinal cord stimulation procedure. The anchor can be deployed onto the trial percutaneous lead from an internal portion of the epidural needle, or can be deployed onto the trial percutaneous lead from an external portion of the epidural needle.

In some examples, the anchor includes an absorbable material that is naturally absorbed by the body after the anchor is deployed onto the trial percutaneous lead such that the anchor does not need to be physically retracted or removed. The absorbable material can include an antibiotic to provide an additional therapeutic effect.

The various embodiments described above are provided by way of illustration only and should not be construed to be limiting in any way. Various modifications can be made to the embodiments described above without departing from the true spirit and scope of the disclosure.

What is claimed is:

1. A percutaneous lead for spinal cord stimulation, comprising:
   a body extending between a distal end and a proximal end;
   at least one contact on the body positioned toward the distal end;
   at least one anchor mounted on the body, the at least one anchor configured to extend between a retracted position and a deployed position to secure the percutaneous lead to tissue outside of an epidural space, wherein the at least one anchor is positioned between the at least one contact and the proximal end, and wherein the at least one anchor is spaced a distance away from the distal end such that the at least one anchor is configured to deploy outside of the epidural space when the at least one contact is positioned adjacent to a target location inside the epidural space; and
   at least one marker visible in fluoroscopy imaging to identify a location of the at least one anchor outside of the epidural space.

2. The percutaneous lead of claim 1, wherein the at least one anchor has a diameter equal to a diameter of the body when in the retracted position.

3. The percutaneous lead of claim 1, wherein the at least one anchor has a diameter two to three times larger than a diameter of the body when in the deployed position.

4. The percutaneous lead of claim 1, further comprising a plurality of anchors, and wherein each anchor of the plurality of anchors is individually controllable to extend between the retracted position and the deployed position.

5. The percutaneous lead of claim 1, wherein the at least one anchor includes a balloon, wherein the balloon is inflatable to have a predetermined diameter in the deployed position, and wherein the balloon is deflatable to return to the retracted position for removal of the percutaneous lead.

6. The percutaneous lead of claim 5, wherein the balloon is inflatable to have a material visible in fluoroscopy imaging.

7. The percutaneous lead of claim 1, wherein the at least one anchor includes a tine configured to extend relative to the body between the retracted and deployed positions.

8. The percutaneous lead of claim 1, wherein the at least one anchor is remotely activated by at least one of Bluetooth, Wi-Fi, RFID, Near-Field Communication, and a magnetic field.

9. The percutaneous lead of claim 1, comprising a plurality of anchors having a unidirectional arrangement such that each anchor of the plurality of anchors is oriented in the same direction when in the deployed position.

10. The percutaneous lead of claim 1, comprising a plurality of anchors having a bidirectional arrangement such that at least two anchors of the plurality of anchors are oriented in different directions when in the deployed position.

11. The percutaneous lead of claim 1, wherein the percutaneous lead is a trial neuro-stimulator lead for spinal cord stimulation.

12. The percutaneous lead of claim 1, wherein the at least one anchor is positioned about 10-40 centimeters from the distal end.

13. The percutaneous lead of claim 1, wherein the at least one anchor is positioned about 20-30 centimeters from the distal end.

14. The percutaneous lead of claim 1, further comprising a plurality of anchors, and each anchor of the plurality of anchors is aligned with a marker of a plurality of markers.

15. The percutaneous lead of claim 14, wherein the plurality of anchors aligned with the plurality of markers are evenly spaced apart by 5 centimeters.

* * * * *